United States Patent
Hirao et al.

(10) Patent No.: US 6,485,725 B1
(45) Date of Patent: *Nov. 26, 2002

(54) ROOM TEMPERATURE STORABLE IMMUNOGLOBULIN PREPARATION FOR INTRAVENOUS INJECTION

(75) Inventors: Yutaka Hirao, Osaka (JP); Motonori Hashimoto, Osaka (JP); Tae Kitamura, Osaka (JP); Yahiro Uemura, Osaka (JP)

(73) Assignee: Welfide Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/564,641

(22) Filed: May 3, 2000

Related U.S. Application Data

(62) Division of application No. 09/177,373, filed on Oct. 23, 1998, now Pat. No. 6,159,471.

(30) Foreign Application Priority Data

Oct. 23, 1997 (JP) .............................................. 9-291374

(51) Int. Cl.$^7$ ............................................. A61K 39/395
(52) U.S. Cl. ................................ 424/176.1; 424/177.1; 530/390.1; 530/390.5; 530/416; 530/421
(58) Field of Search .......................... 424/176.1, 177.1; 530/390.1, 390.5, 416, 421

(56) References Cited

U.S. PATENT DOCUMENTS

| | | | | |
|---|---|---|---|---|
| 4,378,346 A | * | 3/1983 | Tankersley | |
| 4,874,708 A | | 10/1989 | Makula et al. ........... | 424/177.1 |
| 4,876,088 A | | 10/1989 | Hirao et al. .............. | 530/390.5 |
| 4,880,913 A | * | 11/1989 | Doleschel et al. ....... | 530/390.5 |
| 5,132,406 A | | 7/1992 | Uemura et al. .......... | 530/390.5 |
| 5,177,194 A | | 1/1993 | Sarno et al. ................. | 530/421 |
| 6,124,437 A | * | 9/2000 | Hirao et al. .............. | 530/387.1 |

FOREIGN PATENT DOCUMENTS

| | | |
|---|---|---|
| CA | 2185617 | 3/1997 |
| EP | 246579 A2 | 11/1987 |

OTHER PUBLICATIONS

Y. Uemura, et al. "Inactivation and Eliminatin of Viruses During Preparation of Human Intravenous Immunoglobulin" Vox Sanguinis, vol. 67, No. 3, Oct 1994, pp. 246–254.
Database WPI, Week 8943, Derwent Publications Ltd., London, GB: AN 89–312793 XP–002090955 & JP 01 230533 A (The Green Cross Corporation), Sep. 14, 1989.
Database WPI, Week 9518, Derwent Publications Ltd., London, GB: AN 95–136796 XP–002090956 & JP 07 061935 A (The Green Cross Corporation), Mar. 7, 1995.
Database WPI, Week 9625, Derwent Publications Ltd., London, GB: An 96–246917 XP–002090957 & JP 08 099900 A (The Green Cross Corporation), Apr. 16, 1996.

* cited by examiner

*Primary Examiner*—David Saunders
(74) *Attorney, Agent, or Firm*—Sughrue Mion, PLLC

(57) ABSTRACT

A method for producing an immunoglobulin preparation for intravenous injection, which comprises the steps of: fractionating an immunoglobulin-containing solution with 4 to 10 w/v% of polyethylene glycol having a molecular weight of from 1,000 to 10,000, at a pH value of from 4.5 to 6.5, an ionic strength of from 0.0001 to 0.1 M and a temperature of from 0 to 4° C. to recover a supernatant fraction; and concentrating the supernatant fraction at a pH of from 3.5 to 5.0.

5 Claims, No Drawings

ROOM TEMPERATURE STORABLE IMMUNOGLOBULIN PREPARATION FOR INTRAVENOUS INJECTION

This is a divisional of application Ser. No. 09/177,373 filed Oct. 23, 1998, now U.S. Pat. No. 6,159,471 the disclosure of which is incorporated herein by reference.

BACKGROUND OF THE INVENTION

1. Field of the Invention

This invention relates to an immunoglobulin preparation for intravenous injection, more specifically, a room temperature storable immunoglobulin liquid preparation for intravenous injection.

2. Description of the Related Art

Among γ-globulins which are plasma protein components, an immunoglobulin preparation comprising IgG has been used for preventing and treating various infectious diseases. The immunoglobulin is unstable in the form of a solution. It is known that as a result of the aggregation of immunoglobulin, in other words, as a result of the denaturation of the immunoglobulin during the fractionating operation resulting in the formation of a polymer or dimer of immunoglobulin, the immunoglobulin shows a marked increase in the complement-fixing property which is called anticomplementary activity, leading to a) lowering the serum complement concentration upon intravenous administration to a human body or b) serious side effects such as anaphylactic shock. Accordingly, immunoglobulin has been formulated not as a liquid preparation but as a dry preparation, particularly, in a lyophilized form. However, the dry preparation is accompanied with the problem that it cannot be administered easily because of the necessity of dissolving it in distilled water for injection or the like upon use.

On the other hand, the liquid preparation does not require any dissolving operation in distilled water for injection or the like and can be administered easily compared with the dry preparation. As described above, however, it is accompanied with such drawbacks as inferiority in the stability of immunoglobulin. Accordingly, there has conventionally been an attempt to develop a liquid composition of immunoglobulin for intravenous injection having stability even in the form of a solution.

For example, JP-A-63-192724 (the term "JP-A" as used herein means an "unexamined published Japanese patent application" (U.S. Pat. No. 4,876,088, EP 278422)) discloses a liquid immunoglobulin composition for intravenous injection having stability even in the form of a solution, said composition having a low conductivity and pH of 5.5±0.2 and containing sorbitol as a stabilizer.

JP-A-58-43914 (U.S. Pat. Nos. 4,396,608 and 4,499,073, EP 73371) discloses that in order to obtain an immunoglobulin composition which is substantially free of an aggregate of immunoglobulin and has a monomer content of immune serum globulin exceeding about 90%, a solution of the immune serum globulin is adjusted to have an ionic strength less than about 0.001 and a pH of 3.5 to 5.0.

JP-A-9-124507 (EP 764447) discloses a step of lowering ionic strength at pH 3.5 to 5.0 in order to lower anticomplementary activity after a virus inactivation step by tri-(n-butyl) phosphate (TNBP) treatment of immunoglobulin.

JP-A-7-238036 (EP 702960) discloses that for the improvement of stability, the aggregation of immunoglobulin, in other words, an increase of not only a polymer of immunoglobulin but also a dimer of immunoglobulin is suppressed by acid treatment or storage at room temperature.

JP-W-59-501546 (the term "JP-W" as used herein means an "unexamined published Japanese international patent application", WO 84-891) discloses ultrafiltration treatment of an immunoglobulin preparation at pH 5 to 5.6 in the presence of 0.05 to 2 w/v% polyethyleneglycol (PEG).

However, even considering the effects of the steps of the above disclosure, still there is room for improving storage stability of an immunoglobulin preparation, especially, storage stability of an immunoglobulin preparation in the form of a solution.

JP-A-63-8340 (U.S. Pat. Nos. 4,762,714 and 4,948,877, EP 240856) discloses a process for preparing immune serum globulin substantially free of an acquired virus, which comprises obtaining immune serum globulin from the human plasma source by the cold ethanol fractionating method at a pH of about 5.4 or lower and storing the immune serum globulin at a pH of about 4.25 or lower for at least about three days or storing it at a pH of about 6.8 or lower and a temperature of at least 45° C. so as not to contain an infectious retrovirus substantially. However, the above-described invention aims at the inactivation of a retrovirus. It has not been reported that the immunoglobulin preparation thus obtained shows an improvement in the aggregation-wise problem of immunoglobulin.

WO 95-3826 discloses the immunoglobulin preparation comprising 0.1 g/L or less of non-ionic surfactant as stabilizer for maintaining solution state, and being substantially free of albumin. However, the contaminated albumin cannot be detected in accordance with WO 95-3826 when it is in an amount of 1% or less as a relative ratio because of the sensitivity of the measuring method disclosed in said patent.

JP-A-63-183539 (U.S. Pat. No. 5,132,406, EP 246579) discloses a method for the production of immunoglobulin preparations for intravenous injection, which comprises a combination of a heat treatment step, a supernatant fraction recovering step by a fractionation treatment with 4 to 10% PEG and a precipitation fraction recovering step by a 10 to 15% PEG fractionation treatment.

SUMMARY OF THE INVENTION

As described above, immunoglobulin is essentially an unstable protein so that the stability thereof upon preparation of a liquid composition is one of the great concerns.

An object of the present invention is to overcome the above-described problem and hence to provide an immunoglobulin preparation having good storage stability even in the form of a solution.

This and other objects of the present invention have been accomplished by:
(1) a method for producing an immunoglobulin preparation for intravenous injection, which comprises the steps of:
   fractionating an immunoglobulin-containing aqueous solution with 4 to 10 w/v% of polyethylene glycol having a molecular weight of from 1,000 to 10,000, at a pH value of from 4.5 to 6.5 at an ionic strength of from 0.0001 to 0.1 M and a temperature of from 0 to 4° C. to recover an immunoglobulin-containing supernatant fraction; and
   concentrating the supernatant fraction at a pH of from 3.5 to 5.0;
(2) a method for producing the immunoglobulin preparation for intravenous injection according to the above (1)

further comprises at least one, preferably all, of the steps of carrying out a virus inactivation treatment, recovering an unabsorbed fraction by an anion exchange treatment, carrying out a filtration treatment with a porous membrane having an average pore size of from 1 to 100 nm, and recovering an unabsorbed fraction by a contact treatment using colloidal silica; and (3) an immunoglobulin preparation for intravenous injection which is prepared by the above-described production method (1) or (2), particularly an immunoglobulin liquid preparation for intravenous injection which is an immunoglobulin preparation for intravenous injection that contains a chemically unmodified (chemical modification-free) complete molecule type immunoglobulin and has a pH of from 5 to 6 and an electric conductivity of 1 mmho or less (calculated at 8° C.), wherein the preparation can be stored at room temperature for at least 1 year after the production and can maintain an anticomplementary activity at 20 units or less and a dimer content of the immunoglobulin at 7% or less constantly during the storage.

DETAILED DESCRIPTION OF THE INVENTION (1) Starting Material

A fraction containing immunogubulin is used as a starting material. This fraction is not particularly limited in so far as it originates from human serum and contains an immunoglobulin fraction. Specific examples of such as immunoglobulin-containing fraction include Fraction II+III and Fraction II obtainable by ethanol fractionation of Cohn (E. J. Cohn et al., *J. Am. Chem. Soc.*, 68, 459 (1946)), and pastes of immunoglobulin-containing fractions equivalent thereto. The starting material may contain impurities, such as human blood-group antibodies, kallikrein, prekallikrein, IgM, IgG polymers, etc.

(2) Process (a) Polyethylene Glycol (PEG) Treatment

The starting immunoglobulin-containing fraction is treated with a low concentration of PEG, and the supernatant liquor is recovered.

The starting material is first suspended in an appropriate aqueous solvent. At this time, an aqueous solvent at least twice the volume, preferably, at least 5 times the volume of said fraction is used. The aqueous solvent may contain sodium chloride, sodium phosphate, potassium phosphate, acetic acid, sodium acetate, citric acid, sodium citrate, etc.

In addition, preferably, the pH ranges from 4.5 to 6.5, and the ionic strength ranges from 0.0001 to 0.1 M for the aqueous solvent-containing the immunoglobulin.

The resulting suspension is treated with PEG having a molecular weight of from about 1,000 to 10,000, and preferably from about 2,000 to 6,000. The treatment can be carried out, for example, by mixing the suspension and PEG while stirring, usually at a temperature of from 0 to 4° C., for a period of from 30 minutes to 6 hours. Recommended treatment conditions are: a protein concentration of from 1 to 20 w/v%, preferably from 5 to 15 w/v%; a PEG concentration of from 4 to 10 w/v%, preferably from 4 to 8 w/v%; a pH of from 4.5 to 6.5, preferably from 5 to 6; and an ionic strength of from 0.0001 to 0.1 M, preferably from 0.0001 to 0.01 M.

The mixture is then subjected, for example, to centrifugation at 6,000 to 8,000 rpm for 10 to 30 minutes to recover the supernatant liquor.

(b) Concentration Treatment at Acidic pH

In this step, the supernatant fraction obtained in the above treatment (a) is concentrated at a pH of from 3.5 to 5.0 (preferably at pH 4 to 4.5). Specifically, the concentration treatment is carried out using an ultrafiltration membrane having a molecular weight cutoff of about 100,000. This treatment may be carried out under a pressure of from 1 to 10 kg/m².

(c) Anion Exchanger Treatment

This process comprises dissolving an immunoglobulin-containing fraction in an aqueous solvent and contacting the solution with an anion exchanger to recover the non-adsorbed fraction. The treatment with an anion exchanger is particularly effective to remove IgM and/or IgG polymers.

The anion exchanger to be used comprises anion exchanging groups bonded to an insoluble carrier. The anion exchanging include a diethylaminoethyl (DEAE) type, a quaternary aminoethyl (QAE) type, etc., and the insoluble carrier includes agarose, cellulose, dextran, polyacrylamide, etc. They can be bonded in a manner known in the art.

An immunoglobulin-containing precipitate is dissolved in an appropriate aqueous solvent having a pH of from 5 to 7, preferably pH of from 5.5 to 7 and a low ionic strength, and preferably an ionic strength of from 0.0001 to 0.1 M. The aqueous solvent may contain the solutes as described in Process (a) above. The protein concentration of the resulting solution preferably ranges from 1 to 15 w/v%, and more preferably from 3 to 10 w/v%.

The immunoglobulin solution is then contacted with an anion exchanger equilibrated with the same aqueous solvent as used above, either in a batch system or in a continuous system. For instance, batchwise treatment can be carried out by mixing the immunoglobulin solution with an anion exchanger in an amount of from about 10 to 100 ml per ml of the anion exchanger, stirring the mixture at 0 to 4° C. for about 0.5 to 2 hours, and centrifuging the mixture at 6,000 to 8,000 rpm for 10 to 30 minutes to recover the supernatant liquor. Continuous treatment can be effected by passing the immunoglobulin solution through a column of an anion exchanger at a rate of from about 10 to 100 ml per ml of the anion exchanger and recovering the non-adsorbed fraction.

In the present invention, the above Process (c) can be omitted as the occasion demands. However, Process (c) is preferably carried out when IgM or a IgG polymer is present as a contaminant.

(d) Treatment with Porous Membrane

The immunoglobulin preparation according to the present invention includes a preparation from which fine particles which can serve as a nucleus for the formation of insoluble foreign matter have been removed. Examples of removal methods include filtration methods through a porous membrane (for example, in the form of a hollow yarn or a sheet).

No particular limitation is imposed on the material of the porous membrane usable in the present invention. Preferred is regenerated cellulose. Examples of the form of the membrane include a hollow yarn and a sheet, with hollow yarn being preferred. For example, the porous hollow yarn made of regenerated cellulose is prepared preferably from an ammonium cupricellulose solution by the micro phase separation method [*American Chemical Society*, 9:197–228 (1985)].

The average pore size of the porous membrane is 1 to 100 nm, preferably 10 to 75 nm, more preferably 10 to 50 nm, and most preferably 35±2 nm. Its thickness is preferably 35±3.5 μm. The membrane has preferably a multilayer structure. When the porous membrane is in the form of a hollow yarn, its internal diameter is preferably 330±30 μm.

When the porous membrane is in the form of a hollow yarn, it is preferably used in the mode of a module. The module is composed of a porous hollow yarn membrane having preferably a membrane area of 0.001 to 1.0 m², a container to be filled with the membrane and an adhesive to integrate them.

Filtration treatment through the porous membrane is carried out, for example, as follows:

An immunoglobulin fraction is first dissolved in an appropriate aqueous solvent. The aqueous medium is preferred to have a pH of 4 to 7 (more preferably pH 5 to 6) and a low ionic strength (more preferably 0.0001 to 0.1 M). Examples of the aqueous medium include an aqueous solution of sodium chloride, distilled water for injection and an acetate buffer, etc. The immunoglobulin solution thus prepared is preferred to have a protein concentration of 1 to 15 w/v% (more preferably 3 to 10 w/v%) and a pH of 4 to 7 (more preferably 5 to 6).

The immunoglobulin solution thus prepared may contain a pharmaceutically acceptable additive (for example, carrier, excipient, diluent), stabilizer and/or a pharmaceutically necessary component which is used for pharmaceuticals within an extent not impairing the object of the present invention.

Examples of the stabilizer include monosaccharides (for example, glucose), disaccharides (for example, saccharose, maltose), sugar alcohols (for example, mannitol, sorbitol), neutral salts (for example, sodium chloride), amino acids (for example, glycine) and nonionic surfactants (for example, polyethylene glycol, polyoxyethylene-polyoxypropylene copolymer ("Pluronic", trade name), polyoxyethylene sorbitan fatty acid ester ("Tween", trade name)). The stabilizer is preferably added in an amount of about 1 to 10 w/v%.

The above-described immunoglobulin-containing solution is filtered through a porous membrane. The filtration pressure or force at this time is 0.1 to 1 kfg/cm$^2$, preferably 0.1 to 0.5 kgf/cm$^2$, more preferably 0.1 to 0.3 kgf/cm$^2$. The treating temperature is preferably 4 to 50° C.

Examples of the mode of the filtration treatment include the cross flow filtration method (circulation type) in which filtration is effected while a straining rate is given to a liquid and the dead end filtration method (non circulation type) in which filtration is carried out without giving a straining rate. The cross flow filtration method by pressed air is preferably adopted.

The filtration treatment can be carried out plural times. Prior to the above filtration treatment, the immunoglobulin-containing solution may be subjected to another filtration treatment.

The immunoglobulin preparation thus prepared is a preparation from which insoluble fine particles having an average particle size not smaller than 100 nm, preferably not smaller than 75 nm, more preferably not smaller than 35 nm and/or soluble fine particles having a molecular weight larger than that of the immunoglobulin (about 150000), both of which may become a nucleus for forming insoluble foreign matter, have been removed, so that even if the immunoglobulin preparation in the form of a solution is stored at 25° C. for at least 30 days under shaking or at 37° C. for at least 39 days, it does not cause aggregation of immunoglobulin, that is, generation of insoluble foreign matter, and exhibits good storage stability. That is, insoluble foreign matter is not visually observed.

Furthermore, a known method may be used in order to further purify the immunoglobulin. For example, a treatment method in which an immobilized diamino compound is used (for removing kallikrein or prekallikrein) and a treatment method in which an immobilized human blood group substance is used (for removing human blood group antibodies) may be employed (see JP-A-9-176045, U.S. Pat. No. 5,132,406, EP 246579).

According to the present invention, Process (d) can be omitted as occasion demands.

(e) Treatment with Colloidal Silica

This is a method of recovering a non-adsorbed fraction by contact treatment with colloidal silica. This step reduces the amount of serum albumin in the immunoglobulin preparation.

(i) Adsorbent

Examples of the colloidal silica used as the adsorbent include silica gel, light silicic anhydride, diatomaceous earth, acid clay, bentonite, kaolin and magnesium silicate aluminate. Preferably, light silicic anhydride ("Aerosil", trade name; product of Nippon Aerosil Co., Ltd. and "Delipid", trade name; product of Zeta Inc.) are employed.

(ii) Treating Conditions

The purified immunoglobulin is dissolved in an appropriate aqueous solvent. The aqueous medium is preferred to have a pH of 4 to 7 (more preferably 5 to 6) and a low ionic strength (more preferably 0.0001 to 0.1 M). Examples of the aqueous medium include those exemplified above in the treatment with the anion exchanger. The immunoglobulin solution thus prepared is preferred to have a protein concentration of 1 to 15 w/v% (more preferably 3 to 10 w/v%) and a pH of 4 to 7 (more preferably pH 5 to 6).

The immunoglobulin solution thus prepared may contain a pharmaceutically acceptable additive (for example, carrier, excipient, diluent), stabilizer and/or a pharmaceutically necessary component which is used ordinarily for pharmaceuticals within an extent not impairing the object of the present invention.

Examples of the stabilizer include monosaccharides (for example, glucose) disaccharides (for example, saccharose, maltose), sugar alcohols (for example, mannitol, sorbitol), neutral salts (for example, sodium chloride), amino acids (for example, glycine), and nonionic surfactant (for example, polyethylene glycol, polyoxyethylene-polyoxypropylene copolymer ("Pluronic", trade name), polyoxyethylene sorbitan fatty acid ester ("Tween", trade name)). The stabilizer is preferably added in an amount of about 1 to 10 w/v%.

Then, the immunoglobulin solution is subjected to contact treatment with the above-described adsorbent. As the contact treatment conditions to be employed, the adsorbent is used in an amount of 1 to 30 g/liter when the concentration of immunoglobulin is 1 to 100 g/liter (more preferably 10 to 100 g/liter). This treatment can be carried out, for example, by either a batch method or a column method. Among these, a batch method is preferred. In the batch method, mixing and stirring are conducted under conditions, for example, at 5 to 25° C. for about 5 minutes to 1 hour. Then, the supernatant (non-adsorbed fraction) can be recovered by, for example, filtration or centrifugation.

The immunoglobulin preparation from which serum albumin has been removed contains a contaminant of serum albumin in an amount not greater than 10 µg, preferably not greater than 5 µg, per 50 mg of immunoglobulin. Specifically, when the immunoglobulin preparation is in the form of a solution containing 5 w/v% of immunoglobulin, it contains a contaminant of serum albumin in an amount not greater than 10 µg/ml, preferably not greater than 5 µg/ml. The immunoglobulin preparation having such properties exhibits more excellent storage stability than the conventional one. For example, even after storage at 25° C. for at least 30 days under shaking, or even at 37° C. for at least 39 days, the immunoglobulin preparation in the form of a solution is free of insoluble foreign matter. That is, insoluble foreign matter is not visually observed. As the assay of serum albumin in the immunoglobulin preparation, methods known in the art can be employed. Examples include, ELISA method, Mancini's method and nephelometry.

In the present invention, Process (e) can be omitted as occasion demands. However, Process (e) is preferably carried out when serum albumin may be present as a contaminant.

(f) Virus Inactivation Treatment

According to this process, an immunoglobulin-containing fraction is heated in the presence of a stabilizer under such conditions that impurities, e.g., HB virus, AIDS virus, etc., are completely inactivated while minimizing reduction of antibody activities of immunoglobulin. The heat treatment is carried out in a dry state having a water content of 3% or less (i.e., dry heat treatment) or in a dissolved state in the form of an aqueous solution (i.e., wet heat treatment).

The stabilizer which can be used in either the dry or wet heat treatment preferably includes disaccharides (e.g., sucrose, maltose, etc.) and sugar alcohols (e.g., sorbitol, mannitol, etc.).

A recommended amount of the stabilizer to be added is from 0.5 to 5 w/v%, and preferably from 1 to 3 w/v%, in the dry heat treatment, or 10 w/v% or more, and preferably from 10 to 50 w/v%, in the wet heat treatment.

It is desirable that the protein concentration of the immunoglobulin-containing fraction to be heat-treated be adjusted to between 1 and 10 w/v%, and preferably to between 3 and 7 w/v%, for the dry heat treatment, or to between 0.1 to 30 w/v%, and preferably to between 5 and 20 w/v%, for the wet heat treatment.

In the case of the dry heat treatment, after a stabilizer is added to the immunoglobulin fraction, if desired, followed by sterilization by filtration, the water content of the fraction is adjusted to 3% or less, and preferably 1% or less by, for example, freeze-drying. Freeze-drying can be carried out, for example, at a temperature of from 20° to 40° C. for a period form about 24 to 96 hours in vacuo of 0.5 mmHg. Then, the fraction is heated at a temperature of from 50° to 70° C., and preferably at about 60° C., for a period of from 10 to 200 hours, and preferably of from about 50 to 100 hours. Stability of the immunoglobulin during the heating can be ensured by conducting the heat treatment in an inert gas atmosphere, such as nitrogen, argon, helium, etc.

In the case of the wet heat treatment, after the aqueous solution of the immunoglobulin-containing fraction is adjusted to a pH of from 4.5 to 6.5, and preferably from 5 to 6, the solution is heated at 50° to 70° C., and preferably about 60° C., for 10 minutes to 20 hours, and preferably about 10 hours.

If the heat treatment process is dry heat treatment, it is preferably carried out at the final process stage. On the other hand, if it is wet heat treatment, it is preferably carried out for the starting material.

In addition, a further viral inactivation step can be carried out using a solvent detergent procedure with a trialkyl phosphate. The purification degree of the immunoglobulin-containing composition at the time of its contact with the trialkyl phosphate of the present invention is not particularly limited but such a composition purified to a certain level can be used.

Then, the contact with trialkyl phosphate may be carried out in either the isolation step or the purification step for the immunoglobulin.

Though not particularly limited, suitable examples of trialkyl phosphate to be used in the present invention include tri-(n-butyl) phosphate, tri-(tert-butyl) phosphate, tri-(n-hexyl) phosphate, tri-(2-ethylhexyl) phosphate, tri-(n-decyl) phosphate and the like. Particularly preferred trialkyl phosphate is tri-(n-butyl) phosphate (to be referred to as "TNBP" hereinafter). A mixture of two or more trialkyl phosphates may also be used.

Trialkyl phosphate of the present invention may be used in an amount of from 0.01 to 10% (w/v), preferably from about 0.1 to 3% (w/v), based on aqueous solution of immunoglobulin.

The contact with trialkyl phosphate is conducted at 0 to 60° C. (preferably 20 to 40° C.) for 30 minutes or more (preferably 1 to 30 hours, more preferably 3 to 10 hours) and about at a pH of from 6 to 8.

Trialkyl phosphate may be used alone or together with a surface active agent. Preferably, trialkyl phosphate may be used in combination with a surface active agent. The surface active agent may be added to the immunoglobulin containing composition at an optional step before, during or after the composition is contacted with trialkyl phosphate. The function of the surface active agent is to promote contact of viruses in the immunoglobulin-containing composition with the trialkyl phosphate.

Illustrative examples of the surface active agent include polyoxyethylene derivatives of fatty acids and partial esters of sorbitol anhydrides such as Tween 80, Tween 20 and polysorbate 80 and nonionic oil soluble rinsing agents such as Triton X100 (oxyethylated alkylphenol). Also useful are zwittergents which are synthetic zwitter-ion detergents known as sodium deoxycholate and sulfobetaine, such as N-dodecyl-N,N-dimethyl-2-ammonio-1-ethane sulfonate and homologs thereof, and nonionic detergents such as octyl-$\beta$,D-glucopoyranoside and the like.

When the surface active agent is used, its amount is not critical but may be within the range of from about 0.001% to about 10%, preferably from about 0.01% to 3%.

The trialkyl phosphate treatment is especially useful for the inactivation of envelope-coated viruses such as hepatitis B virus, non-A non-B hepatitis virus, human immunodeficiency virus (HIV), vesicular stomatitis virus, sindbis virus and the like.

In the solvent detergent treatment, the immunoglobulin will be present in an amount of about 0.1 w/v to 30 w/v(%), preferably 1 w/v to 20 w/v(%).

(3) Final Preparation (Particularly Liquid Preparation)

(a) Preparation of Liquid Preparation

By using the above-described method for preparing an immunoglobulin preparation for intravenous injection according to the present invention, an immunoglobulin preparation for intravenous injection can be obtained. In a preferred embodiment, a chemical-modification free and complete-molecular immunoglobulin liquid composition (preparation) which can be administered intravenously can be obtained by adjusting an aqueous solution of a chemical-modification free and complete-molecular immunoglobulin to have a concentration of 1 to 10 w/v% (more preferably 3 to 7 w/v%) by the conventional method, adjusting the resulting solution to contain a stabilizer, for example, sorbitol in an amount of 1 to 20 w/v% (more preferably 2 to 10 w/v%), to pH 5 to 6 (more preferably pH 5.5±0.2) and to have a low conductivity (more preferably a conductivity not higher than 1 mmho, more preferably not higher than 0.6 mmho, each calculated in terms of 8° C.) by known methods and then subjecting the resulting solution to sterilizing filtration, pouring in portions and the like based on the ordinary formulating technique.

From the preparation thus formed, an immunoglobulin liquid preparation for intravenous injection which contains chemical-modification free and complete-molecular immunoglobulin, has a pH of 5 to 6 (more preferably about 5.5±0.2) and a conductivity not greater than 1 mmho (more preferably not greater than 0.6 mmho, each calculated in terms of 8° C.), that can be stored at room temperature, has an anticomplementary activity not greater than 20 units and has a content of the dimer of immunoglobulin not greater than 7% can be produced.

The terminology "chemically unmodified and complete molecular type immunoglobulin" as used herein means immunoglobulin possessing the following properties:

(i) It remains intact (natural) without undergoing any artificial modification or change. Therefore, it does not contain immunoglobulin fragments, such as Fab, F(ab')$_2$, Fc, etc.

(ii) It shows neither reduction of antibody titer nor antibody spectrum as compared with intact immunoglobulin.

(iii) Its anticomplementary activity (complement fixation activity) is sufficiently lower than 20 units (CH50 value) which is regarded safe based on Japan Biological Preparation Standard according to Notification No. 159 (October 1985) issued by Ministry of Public Welfare of Japan. (One unit in terms of CH50 is defined as the amount of complement necessary to hemolyze half the amount of $5 \times 10^8$ cells of sensitized erythrocyte in 7.5 ml of a reaction mixture having a certain ionic strength and pH value, and a certain amount of $Ca^{++}$ and $Mg^{++}$ under the reaction of 60 minutes at 37° C.)

When a safety range of the content of the immunoglobulin dimer is taken into consideration with regard to an immunoglobulin-containing preparation for intravenous injection which comprises chemical-modification free and complete-molecular immunoglobulin, the content of the immunoglobulin dimer is set at 7% or below, preferably 6% or below, and most preferably 4% or below.

The preparation according to the present invention has immunoglobulin not substantially inactivated, contains neither an IgG polymer nor contaminant, has good solubility and has sufficiently low anticomplementary action and is a safe preparation which can pass the biological preparation standards when a virus is inactivated, for example, by heating treatment.

The immunoglobulin preparation according to the present invention can be used as is or can be diluted with an appropriate solvent (for example, distilled water for injection, physiological saline, glucose solution) when it is a liquid preparation. When it is a dry preparation, on the other hand, the above-described immunoglobulin solution is lyophilized. It is dissolved in an appropriate solvent (for example, distilled water for injection) upon use.

(b) Examples of Applicable Diseases Treated
1. hypogammaglobulinemia and agammaglobulinemia
2. critical inflammatory diseases
3. secondary thrombocytopenic purpura
4. acute phase of Kawasaki disease (c) Use and Dose The pharmaceutical preparation of the present invention is used by intravenous drip infusion or directly by intravenous injection. When used by direct intravenous injection, it is desirable to carry out the injection extremely slowly.

In general, it is used in an amount of from 2,500 to 5,000 mg as unit dose of human immunoglobulin G for adults, or in an amount of from 100 to 150 mg/kg body weight as unit dose of human immunoglobulin G for children. These dosage ranges are optionally changed depending on the age and symptoms.

When used in secondary thrombocytopenic purpura, it is administered in a dose of generally from 200 to 400 mg/kg body weight per day as human immunoglobulin G. The dosage range is optionally changed depending on the age and symptoms.

When used in Kawasaki disease, it is administered generally for 5 days in a dose of 400 mg/kg body weight per day as human immunoglobulin G. The dosage range is optionally changed depending on the age and symptoms.

According to the present invention, the yield of immunoglobulin and stability of immunoglobulin stored at room temperature can be improved. Furthermore, the production of insoluble foreign matters can be inhibited by removing contaminated albumin and removing fine particles around which form the insoluble foreign matters. Therefore, the present invention can provide a preparation, particularly a liquid preparation, having improved stability of immunoglobulin in a solution state.

The present invention will hereinafter be described more specifically by examples and tests. It should however be borne in mind that the present invention is not limited to or by them.

EXAMPLE 1

To 1 kg of Cohn's fractions II+III obtained from the human plasma by the cold ethanol method, 10 liters of water were added, followed by extraction of IgG. After 50 g of sorbitol were added per 100 ml of the resulting supernatant and its pH was adjusted to 5.5, the resulting mixture was heated to 60° C. for 10 hours. Then, the reaction mixture was adjusted to pH 5.5 and diluted three-fold with cold water for injection. To the diluted liquid, polyethylene glycol (average molecular weight: 4000) was added to give a final concentration of 8 w/v%. The resulting mixture was centrifuged at 2° C. to obtain a supernatant. The thus recovered supernatant was adjusted to pH 4 and then the solution was concentrated against water for injection with an ultrafiltration membrane of 100,000 molecular weight cutoff (Pericon 2 Biomax, manufactured by Millipore). To the resulting solution adjusted to pH 5 to 7, DEAE-Sephadex equilibrated with water for injection was added (about 2 ml per 50 ml of the solution). Under a temperature of 0 to 4° C., the resulting mixture was subjected to contact treatment for about one hour. After the treatment, the DEAE-Sephadex was removed by filtration to recover a filtrate (IgG solution).

The IgG solution thus recovered was diluted into a 5 w/v% solution with water for injection, and its pH was adjusted to about 5.5 with sodium acetate. Sorbitol was then added thereto to give a final concentration of 5%. The aqueous solution thus obtained (conductivity: about 1 mmho) was sterilized by filtration to obtain an immunoglobulin preparation for intravenous administration.

EXAMPLE 2

The solution containing 5 w/v% of immunoglobulin prepared in Example 1 was passed through an anhydrous silica-carrying filter (Zeta Plus Delipid, manufactured by Quno Corp.) to recover the unabsorbed fraction. This was further sterilized by filtration to obtain an immunoglobulin liquid preparation for intravenous injection.

Amount of contaminated albumin in the thus obtained 5 w/v% immunoglobulin-containing-solution was found to be 5 μg/ml when determined by the Mancini's method.

EXAMPLE 3

A porous hollow yarn (Bemberg Microporus Membrane; hereinafter referred to as "BMM") module (trade name: Planova 35) purchased from Asahi Chemical Industry was used, which is produced by modulating the porous hollow yarn (BMM) having an average pore size of 35±2 nm, a membrane area of 0.001 to 1.0 m², a hollow yarn inner diameter of 330±30 μm, a membrane thickness of 35±3.5 μm and a multiple layer structure of 150 layers or more, obtained from cuprammonium regenerated cellulose as the material. This BMM module is integrated, using a polyurethane adhesive, with the inside of a plastic container made of polycarbonate which can be autoclaved, and distilled water for injection use is packed in the module. Safety of each of the Planova-constructing materials has been confirmed by respective methods established by The Pharmacopoeia of Japan (according to the descriptions on BMM).

The solution containing 5 w/v% of immunoglobulin prepared in Example 1 was sterilized by filtration (filtration by a membrane filter having a pore size of 0.2 μm) and then subjected to 1 to 5 hours of a membrane filtration treatment with the Planova 35 module at 5° C. under a filtration pressure of 0.2 kgf/cm² (dead end filtration using air pressure). After cooling, the sterilization treatment was again carried out to prepare an immunoglobulin liquid preparation for injection use.

EXAMPLE 4

The solution containing 5 w/v% of immunoglobulin prepared in Example 1 was passed through a porous/low Al filter (Zeta Plus LA90, manufactured by Quno Corp.) and an anhydrous silica-carrying filter (Zeta Plus Delipid, manufactured by Quno Corp.) to recover the unabsorbed fraction. This was further sterilized by filtration to obtain an immunoglobulin liquid preparation for intravenous injection.

EXAMPLE 5

The solution containing 5 w/v% of immunoglobulin prepared in Example 1 was passed through a porous/low Al filter (Zeta Plus LA90, manufactured by Quno) and an anhydrous silica-carrying filter (Zeta Plus Delipid, manufactured by Quno Corp.) to recover the unabsorbed fraction. After carrying out the BMM treatment in accordance with the procedure of Example 3, this was sterilized by filtration to obtain an immunoglobulin liquid preparation for intravenous injection.

EXAMPLE 6

An immunoglobulin liquid preparation for intravenous injection was prepared in the same manner as described in Example 1, except that the virus inactivation treatment was effected by carrying out 6 hours of contact of the fraction with 0.3 w/v% of TNBP (tri-n-butyl phosphate) and 1 w/v% of polyoxyethylene sorbitan oleic acid monoester (Tween 80) at pH 7 and at 30° C., instead of carrying out 10 hours of liquid state heat treatment at pH 5.5 and at 60° C.

EXAMPLE 7

A powder preparation of immunoglobulin for intravenous injection was prepared in the same manner as described in Example 1, except that freeze drying was carried out by adjusting pH of the fraction to 6.4 to 7.2 and then blending the fraction with 0.6% sodium chloride, 2% mannitol and 1% albumin, instead of preparing the liquid preparation by adjusting to pH 5.5 and blending with sorbitol.

EXAMPLE 8

A powder preparation of immunoglobulin for intravenous injection was prepared in the same manner as described in Example 1 except that, while 10 hours of liquid state heat treatment was carried out at pH 5.5 and at 60° C. in the first step and the liquid preparation was prepared by adjusting the pH to 5.5 and blending with sorbitol in the preparation step in Example 1, the first step liquid state heat treatment was not carried out in Example 8 but, instead of this, freeze drying was carried out in the final step by adjusting pH of the solution to 6.4 to 7.2 and then blending it with 0.6% sodium chloride, 2% mannitol and 1% albumin after which there was carried out 72 hours of heat treatment at 60° C.

Test Example 1

Properties of the immunoglobulin preparations for intravenous injection prepared in Examples 1 to 8 were examined. The powder preparation was examined after dissolved in water for injection.
(1) Appearance
Turbidity of the liquid preparation that is of interest in connection with appearance, was visually observed.
Further, an absorbance at 600 nm was measured to evaluate appearance as turbidity.
(2) Determination of Polymer Content
The content of immunoglobulin polymers based on the total weight of immunoglobulin in the liquid preparation was determined by means of high performance liquid chromatography.
(3) Anticomplement Titer
Measured in accordance with Kabat and Mayer, *Experimental Immunochemistry*, 225 (1961) and Nishioka & Okada, Men-eki no Seikagaku (Biochemistry in Immunology), Vol. 103, Kyoritsu Shuppan (1971). That is, a sample was added to 100 units of complement, and the decrease in units of the complement was measured and taken as the anticomplement titer.
(4) Measles Antibody Titer
Measured in accordance with the hemagglutination inhibition test method (Rosen, L., *Virology*, 13, 139 (1961)), and expressed by an international unit (IU/100 mg).
(5) Electrical Conductivity
Electrical conductivity was measured with conductivity measuring apparatus, CD-35 MII model (M&S Instrument Co).

The liquid preparations for intravenous injection prepared in Examples 1 to 6 had the following properties.
Properties
pH: 5.5
Electrical conductivity: 1 mmho or less (calculated value at 8° C.)
Dimer content: 7 w/w% or less
Polymer content: 0.1 w/w% or less
Anticomplement titer: 20 units/ml or less
Osmotic ratio: about 1 (ratio to isotonic saline)
Appearance: colorless to transparent hypochromic yellow
Measles antibody titer: 40 IU or more
Turbidity: 0.01 or less
After storing the liquid preparation according to the present invention (Example 5) at 37° C. for 40 days, the properties were similar to those before the storage (immediately after the preparation). Accordingly, the preparation according to the present invention is considered to be stable at least one year when stored at room temperature.

The liquid preparations for intravenous injection prepared in Examples 7 and 8 had the following properties.
pH: 6.4 to 7.2
Dimer content: 7 w/w% or less Polymer content: 0.1 w/w% or less Anticomplement titer: 20 units/ml or less Osmotic ratio: about 1 (ratio to isotonic saline)

Appearance: transparent hypochromic yellow or slightly turbid

Measles antibody titer: 40 IU or more

EXAMPLE 9

An immunoglobulin liquid preparation was prepared in the same manner as in Example 1, except that the pH of the final preparation was adjusted to pH 4.25 instead of pH 5.5.

Test Example 2

The properties of the immunoglobulin liquid preparation for intravenous injection prepared in Example 9 were examined in the same manner as in Test Example 1. It had the following properties.

Properties pH: 4.25

Electrical conductivity: 1 to 2 mmho or less (calculated at 8° C.)

Dimer content: 7 w/w% or less

Polymer content: 0.1 w/w% or less

Anticomplement titer: 20 units/ml or less

Osmotic ratio: about 1 (ratio to isotonic saline)

Appearance: colorless and transparent

Measles antibody titer: 40 IU or more

Turbidity: 0.01 or less

EXAMPLE 10

An immunoglobulin liquid preparation was prepared in the same manner as in Example 1, except that the pH of the final preparation was adjusted to pH 5.2 instead of pH 5.5.

Test Example 3

The properties of the immunoglobulin liquid preparation for intravenous injection prepared in Example 10 were examined in the same manner as in Test Example 1 (Lots A–F). It had the following properties.

1) Properties pH: 5.2

Electrical conductivity: 1 mmho (calculated at 8° C.)

Dimer content: 7 w/w% or less

Polymer content: 0.1 w/w% or less

Anticomplement titer: 20 units/ml or less

Osmotic ratio: about 1 (ratio to isotonic saline)

Appearance: colorless to transparent hypochromic yellow

Measles antibody titer: 40 IU or more

Turbidity: 0.01 or less

After storing the liquid preparation according to the present invention (Example 10) at 30° C. for 6 months, the properties were similar to those before the storage (immediately after the preparation).

2) Contaminants

Substances contaminated in the liquid preparation of the present invention (Example 10) were determined. The measuring methods were as follows.

Human serum albumin:

Turbidimetric method

MCP-1 (Human Monocyte Chemotactic Protein-1):

ELISA method

Activated human complement component-3 (C3a):

Radioactivity method using $^{125}$I-arginine

Polyethylene glycol (PEG):

Colorimetry using barium and iodide (*Microchemical Journal*, 20:190–192 (1957)) or gel permeation chromatography.

The results are shown in Table 1 below.

TABLE 1

| Contaminant | Lot A | Lot B | Lot C | Lot D | Lot E | Lot F |
|---|---|---|---|---|---|---|
| HSA ($\mu$g/ml) | 4 | 5 | 5 | 4 | 3 | 3 |
| MCP-1 (pg/ml) | <16 | <16 | <16 | <16 | <16 | <16 |
| C3a ($\mu$g/ml) | 3 | 0.2 | 0.2 | <0.04 | 0.06 | 0.06 |
| PEG (mg/dl) | 1 | 0.3 | 0.2 | 0.5 | 0.2 | 0.1 |

According to the results shown in Table 1, the present invention provides an immunoglobulin preparation for intravenous injection which is stable in the solution state for at least one year at room temperature, and contains at most 5 micrograms ($\mu$g) per ml of HSA (human serum albumin), at most 16 picograms (pg) per ml of MCP-1 (human monocyte chemotactics protein-1), at most 3 micrograms ($\mu$g) per ml of C3a (activated human complement component-3) and at most 1 mg per dl polyethylene glycol.

While the invention has been described in detail and with reference to specific embodiments thereof, it will be apparent to one skilled in the art that various changes and modifications can be made therein without departing from the spirit and scope thereof.

This application is based on Japanese patent application No. Hei 9-291374, the entire content of which is incorporated hereinto by reference.

What is claimed is:

1. An immunoglobulin preparation for intravenous injection which is stable in the solution state for at least one year at room temperature, and contains at most 5 micrograms ($\mu$g) per ml of HSA (human serum albumin), at most 16 picograms (pg) per ml of MCP-1 (human monocyte chemotactic protein-1), at most 3 micrograms ($\mu$g) per ml of C3a (activated human complement-3) and at most 1 mg per dl polyethylene glycol, and which is an immunoglobulin liquid preparation for intravenous injection which contains a chemically unmodified complete molecule immunoglobulin and has a pH value of from 5 to 6 and an electric conductivity of 1 mmho or less (calculated at 8° C.), wherein the preparation can be stored at room temperature for at least one year after its production and can maintain its anticomplement titer at 20 units or less, and the dimer content of the immunoglobulin at 7% or less, constantly during the storage period, and which contains sorbitol as a stabilizer.

2. The immunoglobulin preparation for intravenous injection according to claim 1, which is prepared by carrying out a treatment of a virus inactivation.

3. The immunoglobulin preparation for intravenous injection according to claim 2, wherein the virus inactivation is a wet heat treatment.

4. An immunoglobulin preparation for intravenous injection which is stable in the solution state for at least one year at room temperature, and contains at most 5 micrograms (μg) per ml of HSA (human serum albumin), at most 16 picograms (pg) per ml of MCP-1 (human monocyte chemotactic protein-1), at most 3 micrograms (μg) per ml of C3a (activated human complement-3) and at most 1 mg per dl polyethylene glycol, and which is an immunoglobulin liquid preparation for intravenous injection which contains a chemically unmodified complete molecule immunoglobulin and has a pH value of from 5 to 6 and an electric conductivity of 1 mmho or less (calculated at 8° C.), wherein the preparation can be stored at room temperature for at least one year after its production and can maintain its anticomplement titer at 20 units or less, and the dimer content of the immunoglobulin at 7% or less, constantly during the storage period, and which is prepared by carrying out a virus inactivation treatment wherein the virus inactivation is a wet heat treatment.

5. The immunoglobulin preparation for intravenous injection according to claim 4, which contains a stabilizer.

* * * * *